United States Patent [19]
Sartory et al.

[11] 3,957,197
[45] May 18, 1976

[54] CENTRIFUGE APPARATUS

[75] Inventors: Walter K. Sartory; John W. Eveleigh, both of Oak Ridge, Tenn.

[73] Assignee: The United States of America as represented by the United States Energy Research and Development Administration, Washington, D.C.

[22] Filed: Apr. 25, 1975

[21] Appl. No.: 571,814

[52] U.S. Cl. .................................. 233/4; 233/19 R; 233/27; 210/96 R
[51] Int. Cl.² ........................................ B04B 11/02
[58] Field of Search .......... 233/4, 19 R, 19 A, 20 R, 233/20 A, 27, 46, 16, 26; 210/96, DIG. 23, DIG. 24; 128/214 E

[56] References Cited
UNITED STATES PATENTS 3,489,145  1/1970  Judson et al. .................... 233/19 R
3,829,584  8/1974  Seiberling ......................... 233/19 R Primary Examiner—George H. Krizmanich
Attorney, Agent, or Firm—Dean E. Carlson; David S. Zachry; Allen H. Uzzell

[57] ABSTRACT

A method and apparatus for operating a continuous flow blood separation centrifuge are provided. The hematocrit of the entrant whole blood is continuously maintained at an optimum constant value by the addition of plasma to the entrant blood. The hematocrit of the separated red cells is monitored to indicate the degree of separation taking place, thereby providing a basis for regulating the flow through the centrifuge.

6 Claims, 2 Drawing Figures

CENTRIFUGE APPARATUS

CROSS REFERENCE TO RELATED APPLICATIONS

The present invention is an operation and control method and apparatus for a continuous flow blood centrifuge. The disclosed method is adaptable to any continuous flow blood centrifuge. The disclosed apparatus is an embodiment of the disclosed method adapted to a closed continuous-flow axial-flow blood centrifuge of the type described in commonly assigned copending application of Julian P. Breillatt, Jr., Carl J. Remenyik, Walter K. Sartory, Louis H. Thacker, and William Z. Penland for "Closed Continuous Flow Centrifuge Rotor" Ser. No. 571,667, filed Apr. 25, 1975, which is incorporated herein by reference.

BACKGROUND OF THE INVENTION

This invention was made in the course of, or under, a contract with the Energy Research and Development Administration. It relates generally to the art of centrifugal separation of blood components.

In a continuous flow blood centrifuge, whol e blood enters the centrifuge rotor and is centrifugally separated into three zones within the separation chamber of the rotor, the plasma zone, the white cell zone, and the red cell zone. All of the zones contain some plasma, so each zone is sufficiently fluid to be separately removed from the rotor by pumps. It is the continuous separate extraction of the zones which is the critical consideration in continuous flow blood centrifuges. In the type of centrifuge disclosed in the above-identified commonly assigned copending application, the three zones are separated at the interface by fluid splitting means such as blades. The red cell zone is removed by a fluid splitter blade positioned at the interface between the white cell zone and the red cell zone. The separation chamber is inclined outwardly to aid in the flow of red cell rouleaux (aggregates) along the outer wall of the chamber.

A critical concern in continuous flow blood centrifuges is the position of the interfaces between separated zones. As may be seen by the calculations in the above copending application, the exact design configuration of a particular centrifuge rotor depends upon the properties of the blood to be separated. More particularly, the radial position of the first annular fluid splitting means and the angle of inclination of the separation chamber depend upon, among other things, the hematocrit of the entrant whole blood. Hematocrit being the ratio of the total volume of particles in blood to the total blood volume, it is easily seen that the widths of the separated zones within the centrifuge depends directly upon the hematocrit of the entrant whole blood. It is somewhat impractical to construct a different centrifuge for each range of hematocrit values, so a method of adapting existing centrifuges to a wide range of hematocrit values has long been needed.

DESCRIPTION OF THE PRIOR ART

The rotor of the above copending application is depicted in FIG. 2. The construction involved a rotatable housing 20; a top closure 21 removably screwed to the bowl; a divider ring 22 removably screwed to the lower side of the top closure; a substantially solid rotor core 23 having an axially extending central whole blood inlet passageway 24, said core being removably screwed to the top closure; a face seal lower half 25 fixedly secured to the upper side of the top closure; a plurality of septa 26, fixedly attached to the closure disposed within the upper portion of the whole blood inlet passageway; a central whole blood inlet 27, having a gradually enlarged diameter in the top closure, interconnecting to the central whole blood inlet passageway and the face seal central whole blood port 28; a plurality of lower septa 29, disposed at the lower end of the central whole blood inlet passageway, fixedly attached to the core 23, and extending radially within a full sectional space between the bottom of the core and the bowl. The bowl inside surface and core outside surface are machined to form an annular whole blood separation chamber therebetween. The substantially vertical portion of the separation chamber is flared to a 4° angle with respect to its axis. At a height of about 2.8 inches from the bottom of the 0.080 inch radial cross section separation chamber, the inner wall of the housing is offset outwardly about ½ inch, then continued upward, the convex curvature and concave curvature having a radius of about 0.1 inch. The divider ring 22, 2 inches high and ½ inch thick, is placed so that the inner wall 30 projects centripetally about 0.040 inch with respect to the bowl inner wall 31 at that height. The lower inside edge of the ring is elongated downwardly, forming an annular fluid splitter blade 33. A red cell rouleaux outlet 34 is defined by the lower and outer surface of the ring and outwardly extended centripetal wall of the housing.

The outer wall 32 of the divider ring 22 extends peripherally into the bowl offset wall defining an annular cavity therebetween and providing a passageway for red cell rouleaux to flow upward to a plurality of radially-oriented packed-red cell passageways 35 in the top closure communicating through the face seal with a packed red cell outlet 42.

The inner wall 30 of the divider ring forms a continuation of the separation chamber, extending upwardly at an angle of 4° and joining a plurality of radially-oriented white-cell concentrage passageways 36 in the top closure communicating through the face seal with a white-cell concentrate outlet 43.

The peripheral wall 37 of the rotor core extends vertically upward 0.79 inch above the first annular fluid splitter blade 33 to the top of the core 23 at which the core and the top closure are shaped to form an annular plasma header 38 therebetween. At this vertical level the top closure is shaped to form a second annular phase splitter blade 39 extending centrifugally to within 0.020 inch of the divider ring inner wall 30 and downwardly into the separation chamber. The annular plasma header is joined by a plurality of radially-oriented plasma passageways 40 communicating through the face seal with a plasma outlet 44.

This centrifuge was efficient for only blood within a narrow range of hematocrits. This severely limited its usefulness because blood from human donors has a much wider range of hematocrits. In addition, the rotor had no means for measuring the rate of recovery of red blood cells, which is an indication of the degree of separation taking place within the centrifuge.

SUMMARY OF THE INVENTION

It is an object of this invention to provide a continuous flow centrifugation method and apparatus for separating whole blood having any of a wide range of hematocrits, into red cell, white cell, and plasma zones.

It is a further object of this invention to provide a continuous flow centrifuge apparatus capable of separating whole blood with a high degree of separation, without the need of frequent regulation by a human operator.

It is a further object of this invention to provide a method for regulating a continuous flow centrifuge for separating entrant whole blood into red cell, white cell, and plasma zones.

These and other objects are accomplished in a centrifuge having a whole blood feed line and red cell, white cell, and plasma extraction lines. This invention in its method aspects comprises continuously measuring the hematocrit of the entrant whole blood and continuously regulating the entrant whole blood hematocrit at a selected value within an optimum range of values. The whole blood hematocrit may be regulated by continuously adding plasma from the plasma extraction line to lower the hematocrit of the entrant whole blood, or, in those cases where a donor's hematocrit is below the optimum range, by continuously adding red cell-rich plasma from the red cell extraction line to increase the hematocrit of the entrant whole blood.

This invention also contemplates regulating the flow rate of entrant whole blood to achieve a high degree of red cell recovery by maintaining the hematocrit of the extracted red cell fraction at a selected value within an optimum range of values.

DETAILED DESCRIPTION

It has been found according to this invention that conventional centrifuges as well as that described in the above-identified copending application can be adapted to a wide range of hematocrits by continuously regulating the hematocrit of the entrant blood.

The apparatus of this invention utilizes the electrical conductivity of blood as an aspect thereof. As an aid to understanding the description which follows, the following phenomenological expressions are explained.

At low frequencies, below about 100,000 cycles/sec, the cell membranes of blood cells do not pass an electric current so the only electrical conduction path is through the plasma. Therefore, the conductivity of the blood equals the conductivity of the plasma multiplied by $(1-H_f)$, where $H_f$ equals the feed hematocrit and $(1-H_f)$ equals the volume fraction of plasma in the feed blood. Therefore, $$C_\beta / C_\rho = 1 - H_f$$

where $C_\beta$ = conductivity of the feed blood
and $C_\rho$ = conductivity of the plasma.

Plasma from different donors has different conductivities, so the conductivity of a given blood must be compared to the conductivity of the plasma from that same blood to yield a value proportional to the feed hematocrit. During the operation of a blood centrifuge a stream of separated plasma is available so that its conductivity can be measured and factored out of the above equation.

Figure 1:
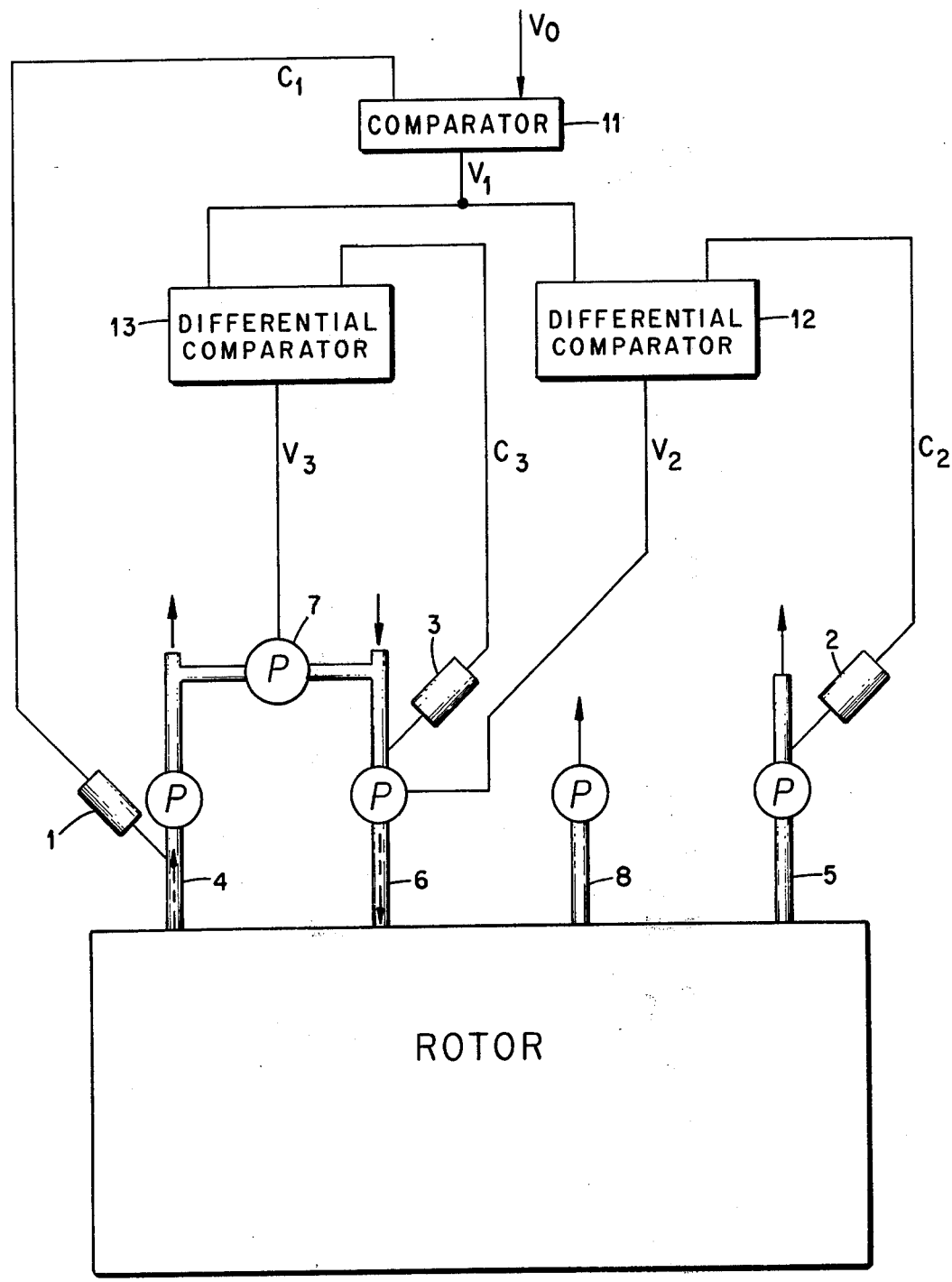
FIG. 1 is a schematic diagram of the hematocrit controlling circuit and the system of pumps.
Figure 2:
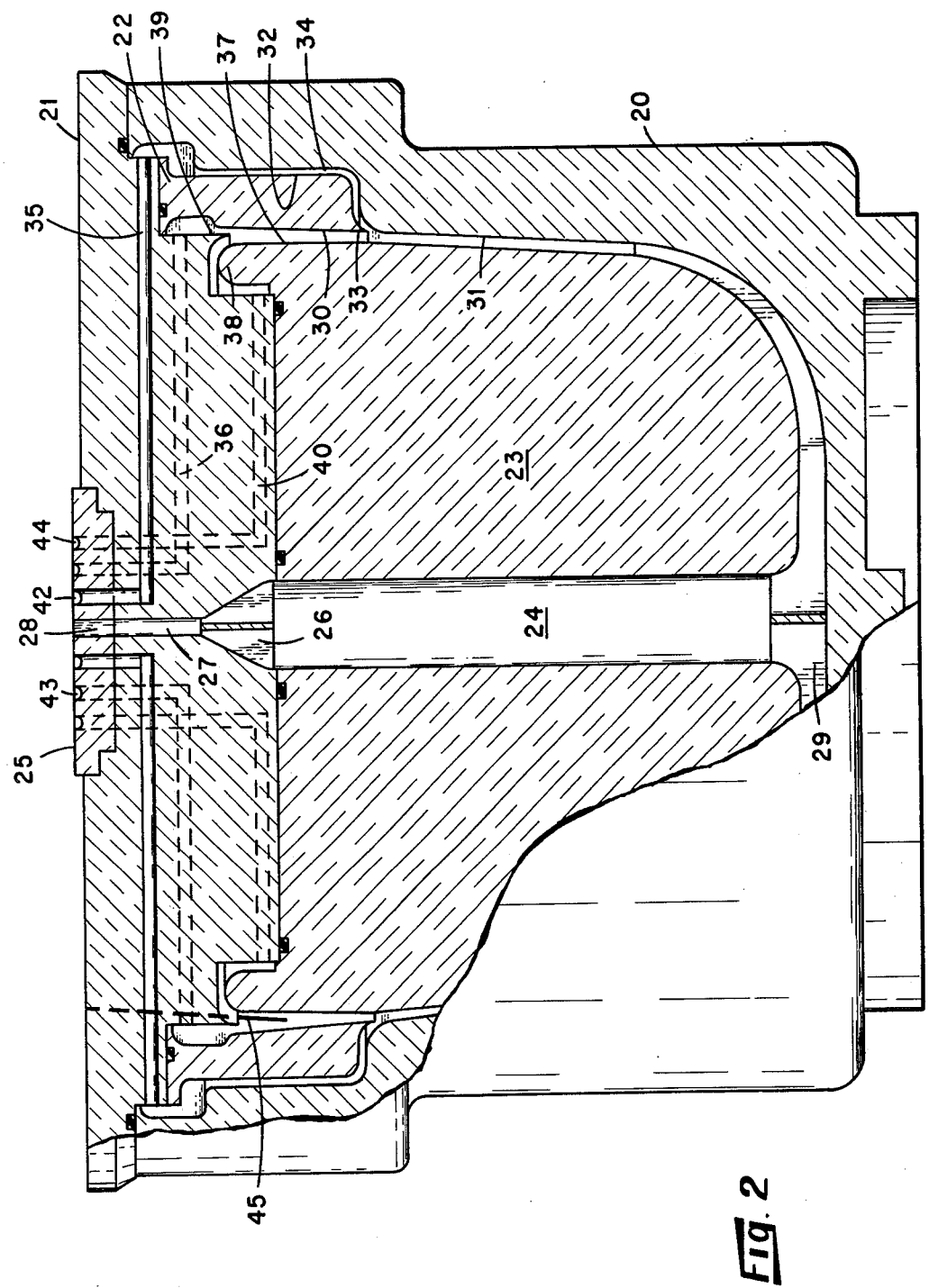
FIG. 2 is a cross sectional view of a prior art centrifuge rotor which is adaptable to control by the method of the present invention.

Referring to FIGS. 1 and 2 in a continuous flow blood centrifuge, whole blood from a donor enters the centrifuge from a whole blood feed line 6 through the central whole blood port 28, and the red cell, white cell, and plasma zones leave the centrifuge through separate extraction lines through the extracted red cell line 5 from packed red cell outlet 42; through the white cell extraction line 8 from the white cell concentrate outlet 43; and through the extracted plasma line 4 from the plasma outlet 44. By disposing conventional conductivity probes within the lines and comparing the conductivity of the entrant whole blood and the extracted red cell zone with the conductivity of the plasma, both the feed hematocrit and the red cell zone hematocrit can be determined.

In accordance with our invention, the electrical conductivities of the entrant whole blood and the plasma are measured and compared to arrive at the value of the feed hematocrit, and plasma is added to the entrant blood to maintain feed hematocrit within an optimum range.

A plasma recycle line interconnecting the plasma extraction line and the whole blood feed line, and a variable speed recycle pump disposed in the recycle line provide a means for diluting entrant blood with plasma to yield feed hematocrit substantially equal to a predetermined optimum feed hematocrit. For purposes of this discussion, the optimum feed hematocrit value is defined as that feed hematocrit value which will yield the greatest degree of red cell and white cell separation in a particular centrifuge rotor. The optimum feed hematocrit value is a function of the design of a rotor. The optimum feed hematocrit value for a given rotor of the subject type is that value which will result in the greatest white cell recovery and may be found by routine experimentation.

The conductivity of the entrant whole blood is differentially compared with the conductivity of the plasma by conventional electronic circuits to provide a d.c. signal to control the variable speed recycle pump, enabling the feed hematocrit to be maintained at the optimum value.

Our invention also includes the method which comprises the steps of measuring the conductivities of the extracted red cell and plasma zones, comparing those values to obtain the value of an extracted red cell hematocrit, and varying the rate of whole blood feed to maintain the extracted red cell hematocrit at a selected value within an optimum range.

The hematocrit of the extracted red cell stream influences the the degree of separation taking place within the centrifuge. For a given rotor operating at a given speed with a given feed hematocrit, there exists an optimum value for extracted red cell hematocrit. This optimum value corresponds to maximum recovery of red cells with minimum presence of white cells in the red cell recovery line. This value may be experimentally determined for a given rotor by fixing the rotor speed and the optimum feed hematocrit and varying the rate of blood flow until optimum red cell recovery is achieved. The hematocrit of the extracted red cell zone will then be the optimum red cell hematocrit. This hematocrit value may be maintained by continuously measuring the hematocrit of the extracted red cell fraction and varying the speed of a variable speed feed pump disposed in the whole blood feed line. This continuous control is necessary because the erythrocyte sedimentation rate may vary slightly requiring variations in the feed rate to achieve maximum recovery. Electronic circuitry differentially comparing the conductivity of the extracted red cell stream with the conductivity of the plasma provides a signal to control the variable speed feed pump, whereby the extracted red cell hematocrit is maintained at its optimum value.

As indicated in FIG. 1, the comparator 11 supplies an output voltage $V_1$ directly proportional to the constant input voltage $V_0$ and the plasma conductivity $C_1$ as measured by the conductivity probes 1 disposed in the extracted plasma line 4. This plasma circuit output voltage $V_1$ serves as a reference input voltage to the hematocrit controlling differential comparators 11 and 12. The output voltage $V_2$ of differential comparator 12 is directly proportional to $V_1$ and to the extracted red cell conductivity $C_2$ as measured by the conductivity probe 2 disposed in the extracted red cell line 5, $V_2$ controlling the feed pump rate, thereby controlling the red cell output. $V_2$ can be alternatively used to control the speed of the centrifuge drive motor; however, the forces associated with increased speeds of the centrifuge are destructive to the red cell rouleaux necessary for complete separation of blood components. The output voltage $V_3$ from differential comparator 13 is directly proportional to $V_1$ and the conductivity $C_3$ as measured by the conductivity probe 3 disposed in the whole blood feed line 6, $V_3$ controlling the plasma recycle pump thus controlling the feed blood hematocrit.

The variable pumps used in this method may be peristaltic tubing pumps available as model 4-6901A Precision Peristaltic Pumps from American Instrument Company, Silver Spring, MD. The rotary driving means may be a model 4-6900 Continuous Flow Celltrifuge, also available from American Instrument Company. The conductivity probes are Radiometer model CPC 114 available from the London Company, Westlake, Ohio, and are operated at 0.25 volt. The rotor is of the type described in the above-mentioned copending application.

What is claimed is:

1. The method of operation of a continuous flow centrifuge for separating entrant whole blood into a red cell fraction, a white cell fraction and a plasma fraction, said centrifuge including a feed line for said entrant whole blood and extraction lines for each of said fractions, said method comprising continuously measuring the hematocrit of entrant whole blood in said feed line and continuously adding a separated fraction from one of said extraction lines to said feed line to continuously regulate the entrant whole blood hematocrit at a selected value.

2. The method of claim 1 wherein said entrant whole blood hematocrit is regulated by continuously adding plasma from said plasma extraction line to said feed line to lower the hematocrit of said entrant whole blood.

3. The method of claim 1 wherein said entrant whole blood hematocrit is regulated by continuously adding red cell rich plasma from said red cell extraction line to said feed line to increase the hematocrit of said entrant whole blood.

4. The method of claim 1 further comprising continuously measuring the hematocrit of the fraction in the red cell extraction line and varying the feed rate of said entrant whole blood to maintain the hematocrit of the extracted red cell fraction at a selected value.

5. In combination with a continuous-flow centrifuge for separating whole blood into a red cell fraction, a white cell fraction, and a plasma fraction, said centrifuge including a feed line for whole blood and extraction lines for each of said fractions, and a recycle line connecting said plasma extraction line to said feed line, a control system comprising:
   a. respective pumps located in said feed line, said plasma line, and said recycle line;
   b. respective electrical conductivity measuring means disposed within appropriate lines for producing first and second electrical signals proportional to the conductivities of said plasma fraction and said whole blood;
   c. means for comparing the magnitude of said first and second electrical signals to produce a first control signal;
   d. first speed control means associated with said pump located in said recycle line; and
   e. means connecting said first control signal to said first speed control means whereby said recycle pump maintains the hematocrit of said whole blood in said feed line at a selected value.

6. The combination of claim 5 wherein said control system further comprises:
   a. electrical conductivity measuring means disposed within said red cell extraction line for producing a third electrical signal proportional to the conductivity of said red cell fraction;
   b. means for comparing the magnitude of said first and third electrical signals to produce a second control signal;
   c. second speed control means associated with said pump located in said feed line; and
   d. means connecting said second control signal to said second speed control means whereby said feed pump maintains the hematocrit in said red cell extraction line at a selected value.

* * * * *